(12) United States Patent
Said et al.

(10) Patent No.: US 7,450,235 B1
(45) Date of Patent: Nov. 11, 2008

(54) OPTICAL SENSING OF FLUID CONDITION-METHOD AND APPARATUS

(75) Inventors: Ali A. Said, Ann Arbor, MI (US);
Philippe Bado, Ann Arbor, MI (US);
Mark Allen Dugan, Ann Arbor, MI (US)

(73) Assignee: Translume, Inc., Ann Arbor, MI (US)

( * ) Notice: Subject to any disclaimer, the term of this patent is extended or adjusted under 35 U.S.C. 154(b) by 542 days.

(21) Appl. No.: 11/037,625

(22) Filed: Jan. 18, 2005

(51) Int. Cl.
*G01N 21/00* (2006.01)

(52) U.S. Cl. .................................. 356/436; 356/432
(58) Field of Classification Search ......... 356/432–438, 356/70–73.1, 337–343, 73; 324/698
See application file for complete search history.

(56) References Cited

U.S. PATENT DOCUMENTS

| | | | |
|---|---|---|---|
| 3,787,703 A * | 1/1974 | Topol | ............................ 250/574 |
| 5,644,239 A | 7/1997 | Huang et al. | |
| 6,151,108 A | 11/2000 | Kwon et al. | |
| 6,628,877 B2 | 9/2003 | Dugan et al. | |
| 6,768,850 B2 | 7/2004 | Dugan et al. | |
| 6,810,718 B2 * | 11/2004 | Wilson et al. | ............... 73/54.01 |
| 6,825,921 B1 * | 11/2004 | Modlin et al. | ................... 356/73 |
| 7,236,237 B2 * | 6/2007 | Schmilovitch et al. | ......... 356/73 |
| 2005/0122522 A1 * | 6/2005 | Padmanabhan et al. | ..... 356/436 |

OTHER PUBLICATIONS

A. Basu et al. "Smart sensing of oil degradation and oil level measurements in gasoline engines" SAE 2000-01-1366.

* cited by examiner

*Primary Examiner*—Tri T Ton
(74) *Attorney, Agent, or Firm*—Lempia Braidwood LLC

(57) ABSTRACT

The invention relates to an apparatus and a method to monitor the condition of a fluid by measuring multiple optical properties of the fluid. The apparatus comprises of a body 105, at least one fluidic cavity 110 to capture a fluid sample, at least one light source 115 to emit an optical signal and at least one optical detector 120 to detect the optical signal. The fluid sample is collected continuously from a path of a fluid flow and multiple optical properties are measured in real time to determine the condition of the fluid. The apparatus is installed in-line with the path of the fluid flow in the system for which the fluid is being used and monitored. The apparatus avoids environmental contamination and wastage of the fluid sample by returning the fluid sample back into the fluid flow.

26 Claims, 10 Drawing Sheets

OPTICAL SENSING OF FLUID CONDITION-METHOD AND APPARATUS

This invention was made with government support under contract No. W56 HZV-04-C-009 awarded by TACOM. The government has certain rights in the invention.

FIELD OF THE INVENTION

The present invention relates to a method and apparatus for determining a condition of a fluid by multiple optical means. More specifically, the invention pertains to sensing the condition of industrial fluids used in various industrial systems.

BACKGROUND OF THE INVENTION

Measuring the condition of a fluid used in a system is indicative of a variety of parameters that can affect the system. More so, measuring the condition of industrial fluids is highly important in industrial systems as it can lead to potentially high risk-involving circumstances. Industrial fluids like engine oil, hydraulic oil and lubricants are used in industrial systems ranging from automobile engines to large plants like petrochemical plants, power plants, metallurgical plants and to various other processes like mechanical processes, thermal-mechanical processes etc. Any unexpected failure or an accidental damage resulting from failure of or presence of impurities in such fluids can result in a hazardous situation. Technologies are required to constantly monitor these fluids. Several methods, including electrical, magnetic and optical are used to assess the condition of the fluid.

There are many electrical or magnetic devices available to monitor the condition of a fluid as described in prior art reference "Smart sensing of oil degradation and oil level measurement in gasoline engines", by Amyioo Basu et al. SAE 2000. However, the information that can be deduced about the condition of the fluid using electrical and magnetic methods is limited. On the other hand, there are not many devices available to monitor the condition of the fluid through optical means. Such devices that are available are complex in design, bulky, difficult to operate, expensive and sensitive to vibrations that occur in industrial systems. Also, there is no option of monitoring the fluid condition continuously with respect to time. In most devices, measurements are made periodically by ejecting samples of fluids using complicated arrangements of pumps and valves.

In prior art reference U.S. Pat. No. 6,151,108, an apparatus to optically monitor the condition of the fluid using optical fibers is disclosed. The apparatus collects samples continuously using pumps and valves and guides an input optical signal through optical fibers and monitors the output. There is however, a time lag involved in monitoring the condition and hence exists the possibility of having skewed information about the condition of the fluid. The setup also involves a complex integration of pumps and valves making the apparatus bulky.

U.S. Pat. No. 5,644,239 discloses electrical and thermal methods to monitor the condition of the fluid, which are supported by optical methods. However, there is no emphasis on the use of optical methods or on making the measurements in real time.

Another prior art reference U.S. Pat. No. 6,825,921 discloses use of a multi optical property measurement system and claims use of at least two of absorption, luminescence, and scattering methods. However, the samples are observed only once as this is directed towards medical applications and the method is not operating under real time.

The present invention eliminates use of bulky devices for optical methods, the invention can easily be integrated in-line with the path of the fluid flow in the system it is being used. Placing the apparatus in-line with the fluid flow in the industrial system to capture the fluid sample and not hindering flow of the fluid sample enables the apparatus to make measurements continuously in real time. By collecting samples through an in-line integrated system, the problem of incorrect sampling, which might not be indicative of the actual condition of the bulk of the fluid, is also eliminated. The invention also makes use of measuring multiple optical methods simultaneously to monitor the condition of the fluid in order to determine accurately the condition of the fluid and to qualitatively predict the impurities present in the fluid.

DETAILED DESCRIPTION OF THE DRAWINGS

The present invention may be embodied in several forms and manners. The description provided below and the drawings show exemplary embodiments of the invention. Those of skill in the art will appreciate that the invention may be embodied in other forms and manners not shown below. The invention shall have the full scope of the claims and is not to be limited by the embodiments shown below.

The invention relates to a method and apparatus for monitoring and sensing the condition of a fluid, more specifically, an industrial fluid used in industrial systems like automobile engines, industrial plants and industrial processes. A few examples of such fluids can be engine oils, hydraulic oils and lubricants etc.

It has been a widely accepted fact that the condition of the fluid used for industrial purposes can be sensed and monitored to a satisfactory level using optical means alone. Although, optical means might not always be able to quantitatively define the contaminants and the contamination level of the fluid, it is however sufficient to obtain a qualitative analysis of the condition of the fluid to be able to avoid the potentially hazardous situations that might arise due to the contaminated fluids prolonged use in the industrial systems.

The invention relates to a method and an apparatus that can be used to monitor the condition of the fluid continuously in real time. The apparatus enables to constantly measure multiple optical properties of the fluid. This enables the apparatus to qualitatively sense the contamination levels as well as the particulates and other contaminating fluids that might be present in the fluid under observation.

In view of the complexity of the apparatus available in the market that use optical means to sense the condition of the fluid, the current invention simplifies the integration of the sensing process with the system it is being used for. The apparatus can further enable integration in-line with the path of the fluid flow being used in the industrial system, to continuously tap fluid samples, perform measurements in real time and return the observations to the user in real time as well. The apparatus also avoids wastage and environmental contamination by returning the fluid sample back to the fluid flow.

Figure 1:
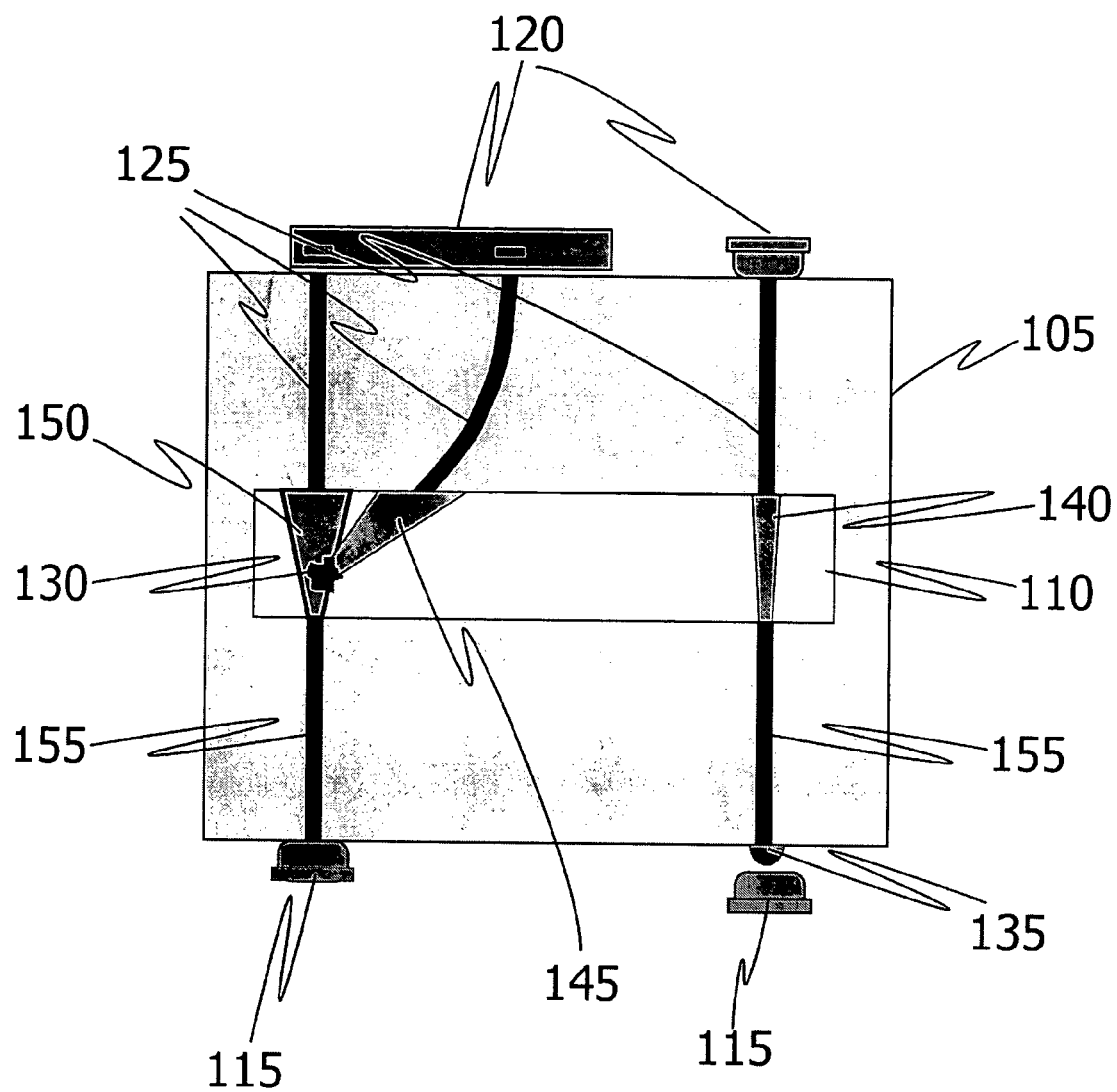
FIG. 1 is a schematic diagram of the working of a preferred embodiment of the apparatus.

FIG. 1 is a schematic diagram of the working of a preferred embodiment of the apparatus. In a preferred embodiment of the invention, the apparatus is used to measure a condition of a fluid used in industrial systems like automobile engines, industrial plants and industrial processes. A few examples of such fluids can be engine oils, hydraulic oils and lubricants etc. A substrate 105 made of glass forms a body of the apparatus that is used to sense the condition of the fluid. The substrate 105 can also be potentially made from polymer, fused silica and silicon with over-layers of fused silica. The substrate 105 is optically transparent for a range of wavelengths between which an optical signal is emitted by a light source 115. In one preferred embodiment of the apparatus, the optical signal can be guided to a fluidic cavity 110 using at least one wave guide 155. In another embodiment of the apparatus, a fluid sample is collected from a fluid flow to monitor the condition of the fluid. In one embodiment of the invention, the fluid sample is taken from a normal path of the fluid flow in the industrial system. For example, there are some industrial systems where there is a clear continuous flow like oil pumped through a filter, or there are other industrial systems the fluid moves only when a force is applied to or removed from the fluid. The optical signal is allowed to pass through the fluid sample present in the fluidic cavity 110. In another preferred embodiment of the apparatus, a lens 135 is used to intensify the optical signal emitted by the light source 115. The lens 135 can also be used to collect the optical signal emitted by the light source 115. In another embodiment of the apparatus, the light source 115 can be a Light Emitting Diode or a Diode Laser. In case of the fluid sample being uncontaminated, the optical signal passes through the fluid sample in the fluidic cavity without getting scattered 140. In the case of the fluid sample being contaminated with a particulate impurity 130, part of the optical signal that falls on the particulate impurity gets scattered 145 and the other part of the optical signal passes through the fluid sample in the fluidic cavity without getting scattered 150. The optical signal, after passing through the fluidic cavity is captured by an optical detector 120. The optical detector 120 measures multiple optical properties of the fluid sample by sensing the captured optical signal. In another embodiment of the apparatus, the optical signal after passing through the fluid sample in the fluidic cavity is guided to the optical detector using wave guide 125. The optical detector 120 measures a first Luminous intensity value change of the optical signal that has passed through the fluid sample in the fluidic cavity 110 without being scattered. This can also be perceived as measuring an Absorption value of the optical signal. The optical detector 120 further measures a second Luminous intensity value change for the optical signal that has scattered after falling on the particulate impurity. A Luminous intensity change signifies a change in the 'Candela' value of the optical signal emitted by the light source 115 as compared to the 'Candela' value of the optical signal captured by the optical detector 120. The luminous intensity change can signify a change in a unit value of the optical signal or even the 'Lumen' value of the optical signal.

Figure 2:
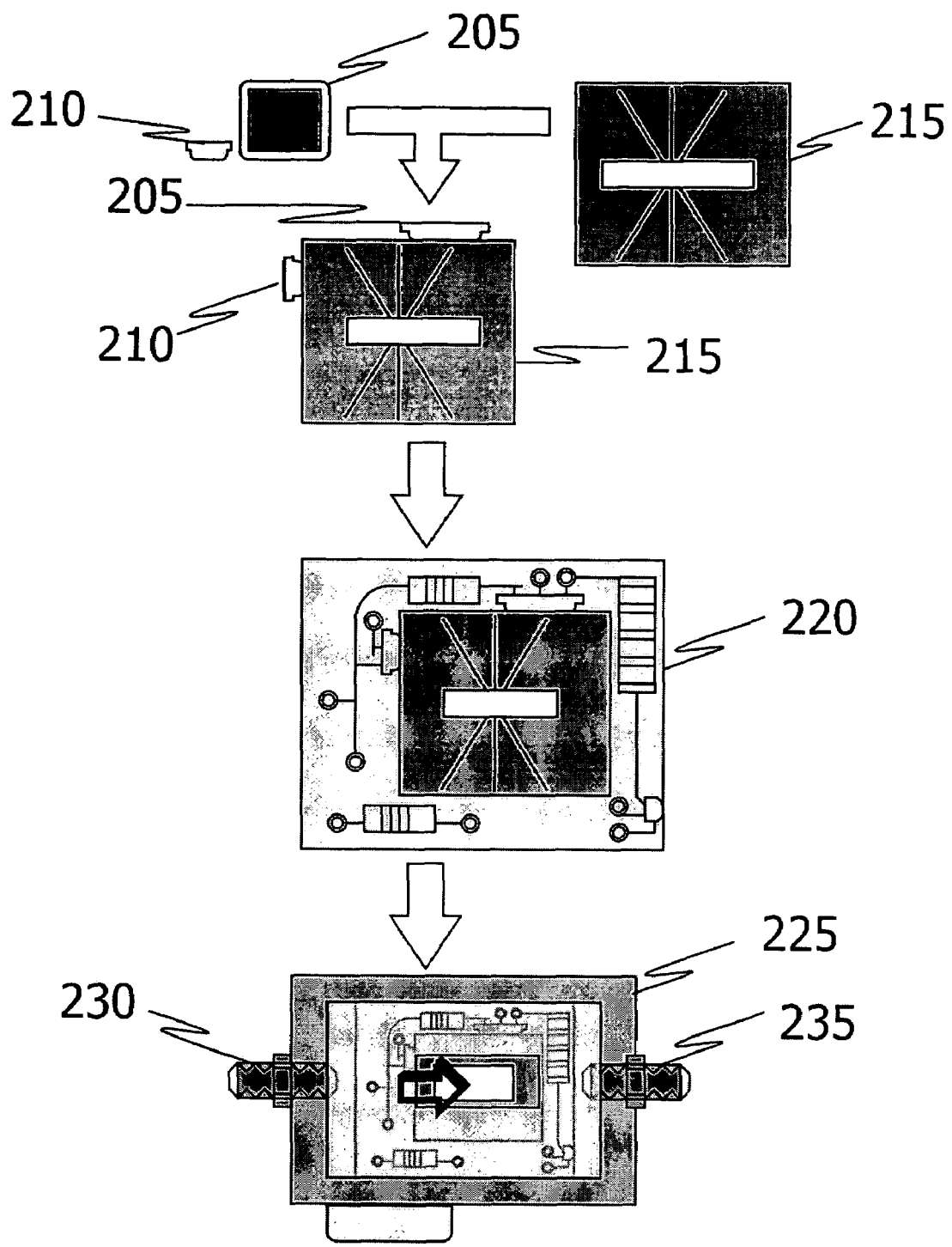
FIG. 2 is a process flow diagram for the assembly of the apparatus.

FIG. 2 is a process flow diagram for the assembly of the apparatus. In a preferred embodiment of the apparatus, optical-electronic components like the light source 210 and the optical detector 205 are assembled with a substrate formed of glass 215 that contains a fluidic cavity and at least one wave guide. In another preferred embodiment of the apparatus, assembly is done by aligning and bonding the light source 210, the optical detector 205 with the substrate 215 using processes like soldering and machining etc. This assembly is further packaged along with the signal conditioning board 220 that is used to electronically control the light signal emitted from the light source. In another embodiment of the apparatus, the signal conditioning board 220 is also used to send an electronic feedback from the optical detector to the light source to maintain consistency in the luminous intensity, i.e. the 'Candela' value of the optical signal emitted by the light source. In another embodiment of the apparatus, the packaged apparatus 225 has an inflow to the fluidic cavity 230 for the fluid sample and an outflow from the fluidic cavity fluidic 235 for the fluid sample. In another embodiment of the invention, there can be only one opening to the fluidic cavity for the fluid sample. The packaged apparatus 225 can be integrated in-line with a fluid flow in the industrial system for which the fluid is being used. The apparatus can be attached in-line with a fluid flow. Thereby, the fluid sample that is collected in the fluidic cavity is taken from a normal path of fluid flow used in the industrial system. For example, there are some systems were there is a clear continuous fluid flow like oil pumped through a filter. In such cases, the fluid sample will be continuously collected in the fluidic cavity while the fluid is in motion, giving an in-line arrangement of sensing the fluid condition in real time. There are also some systems where the flow is not continuous, such as Hydraulic brake systems wherein the hydraulic fluid moves only when a force is applied to or removed from the brake pedal. Here, the fluid sample is collected in the fluidic cavity whenever the fluid is set into motion, giving an in-line arrangement of sensing the condition of the fluid in real time. Besides this, the fluid may also be present in the cavity when the fluid is not moving through the apparatus. On the other hand, fresh fluid is brought into the cavity when the fluid is set into motion. The measurements are made while the fluid sample is flowing in the fluidic cavity and the fluid sample is ejected back into the normal path of the fluid flow after the fluid sample has flown out through the outflow 235 from the fluidic cavity.

Figure 3:
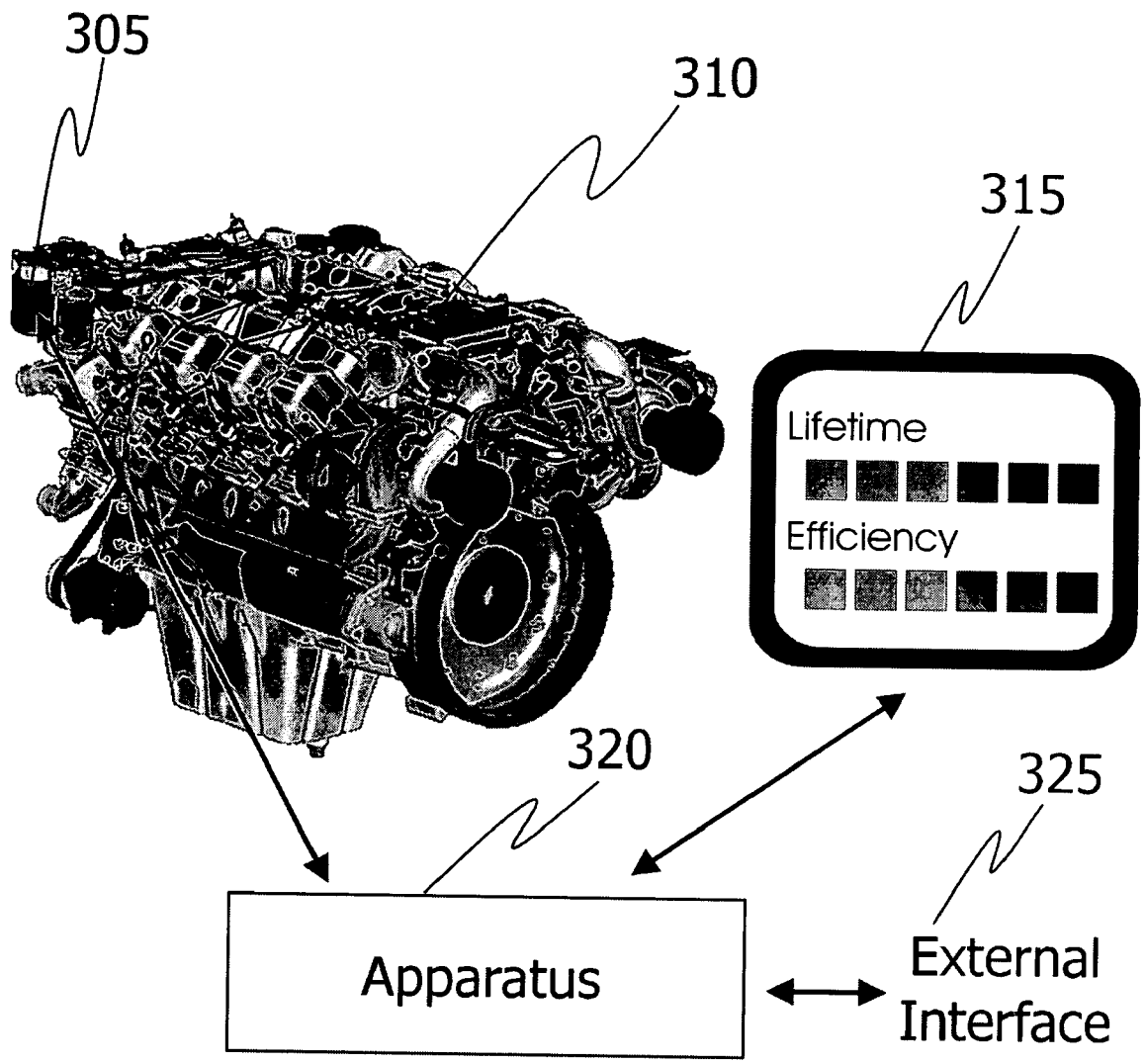
FIG. 3 is a schematic diagram of an embodiment of the apparatus wherein the apparatus is installed in-line with an engine.

As per another embodiment, as shown in FIG. 3, which is a schematic diagram wherein the apparatus is installed in-line with the filter 305 of an engine 310. The engine oil flows through the filter of the engine, and normal course of flow passes through the fluidic cavity within the apparatus 320 that is integrated in-line with the filter. At any given instance of time the amount of fluid passing through the fluidic cavity constitutes the fluid sample. The apparatus thus performs the monitoring in real time by measuring the required optical properties of the fluid sample while it flows through the fluidic cavity. The fluid sample joins the normal course of the fluid flow as it flows out of the fluidic cavity. A user can see an external interface 325 of the apparatus that displays the condition of the fluid based on measurements of the optical properties of the fluid sample. Additionally, data including the condition of the fluid can also be transferred to a remote center or to a remote user using wireless technology. In another embodiment, the external interface 325 displays quality of the fluid in terms of 'Lifetime' and 'Efficiency' of the fluid 315.

Figure 4:
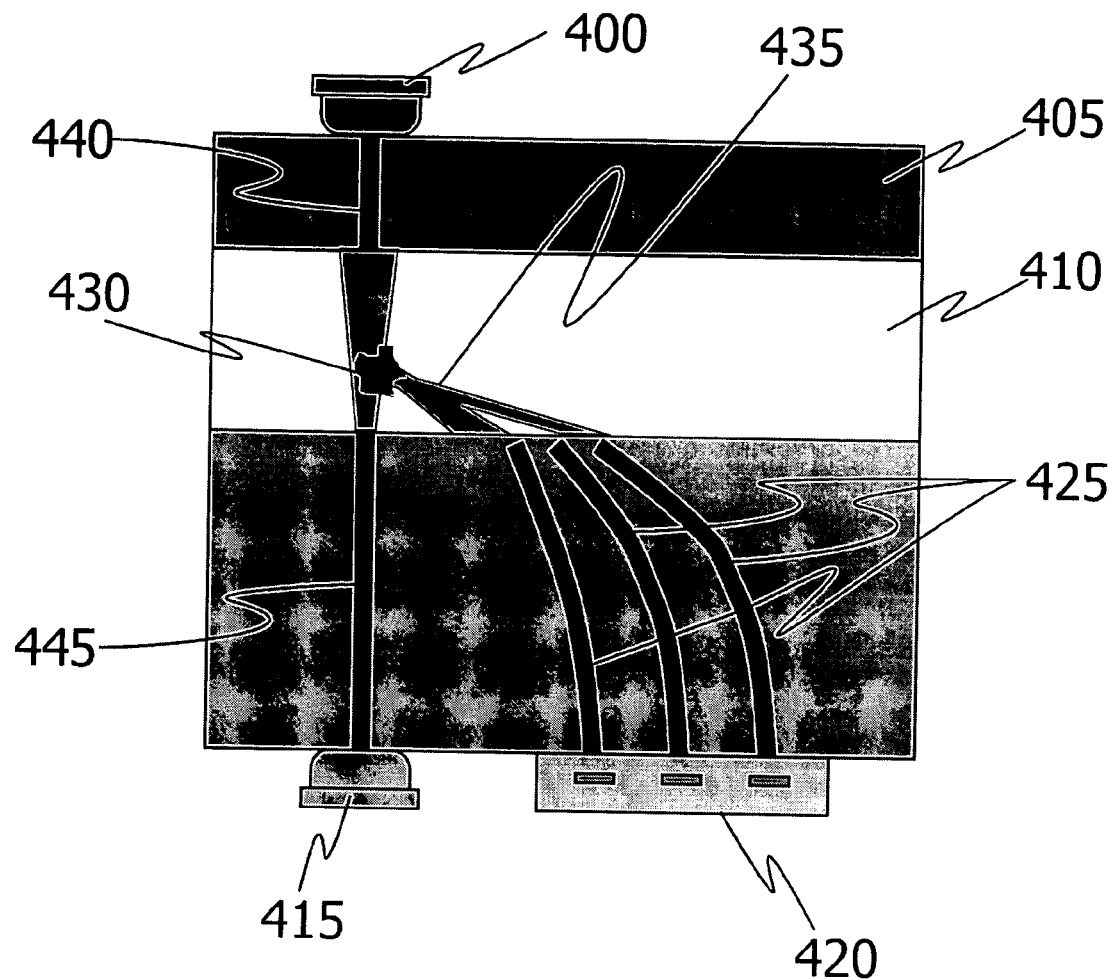
FIG. 4 is a schematic diagram for an embodiment of the apparatus demonstrating back scattering measurement.

In another embodiment of the apparatus, as shown in FIG. 4, which is a schematic diagram for an embodiment of the apparatus demonstrating angular scattering detection. The optical signal emitted by a light source 415 gets scattered at an acute angle due to a particulate impurity 430 in the fluid sample flowing through a fluidic cavity 410. The fluidic cavity is contained in a glass substrate 405 that constitutes the body of the apparatus and the optical signal is guided from the light source to the fluidic cavity using at least one wave guide 445. Scattering at an acute angle results in back scattering of the optical signal 435. In another embodiment of the apparatus, the back scattered optical signal 435 is guided through a wave guide 425 to an optical detector 420 that measures a Luminous intensity change in the backscattered optical signal 435. A part of the optical signal that does not scatter is guided by at least one wave guide 440 to an optical detector 400. In another embodiment of the apparatus, backscattered optical signal 435 as well as the scattered optical signal 145 as shown in FIG. 1 may simultaneously coexist.

Figure 5:
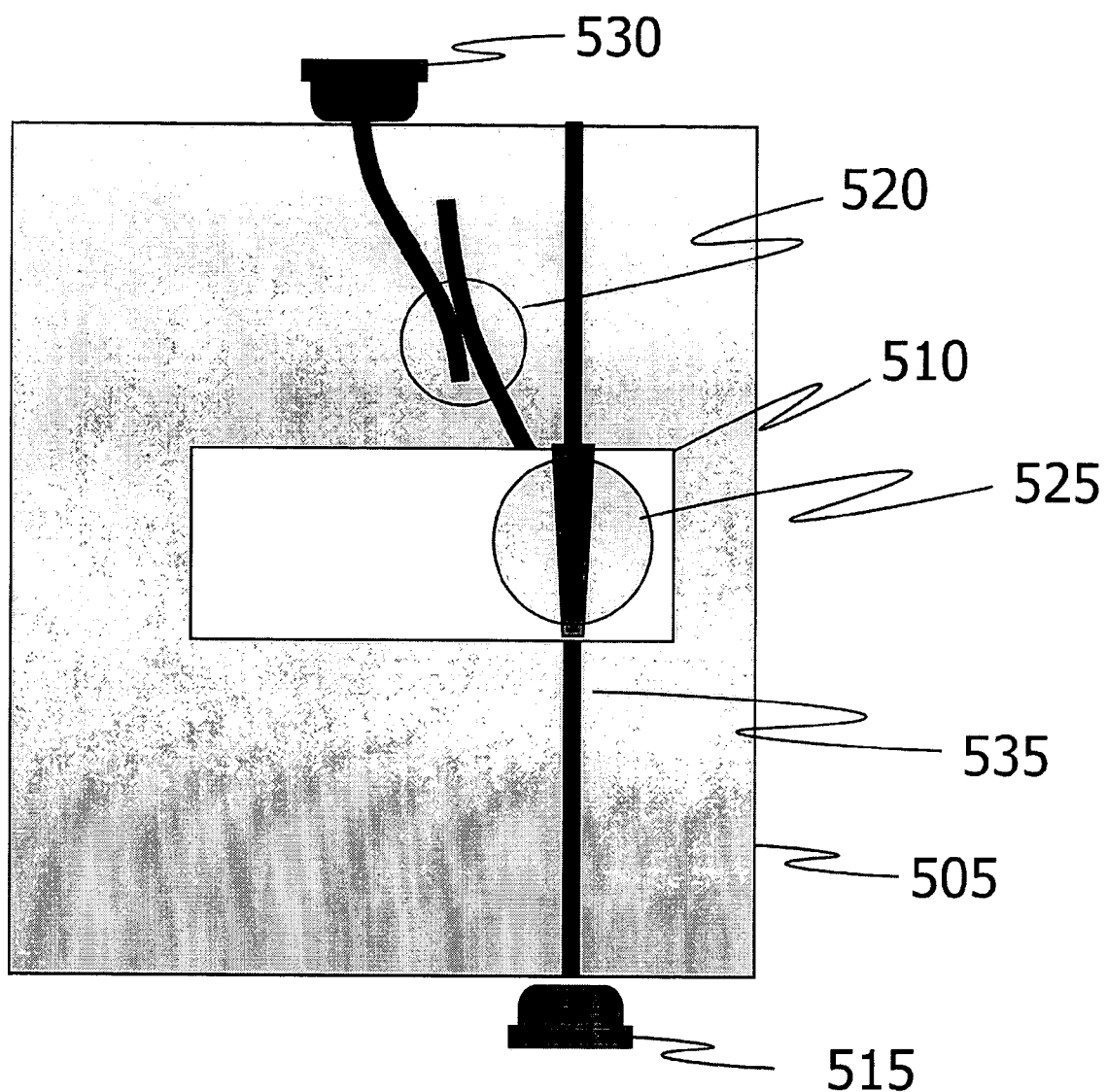
FIG. 5 is a schematic diagram for another embodiment of the apparatus demonstrating fluorescence measurement.

As per another embodiment of the invention, as shown in FIG. 5, fluorescence of the fluid can be measured to assess the fluid. Such measurements can provide information about contaminants within the fluid that fluoresce when illuminated, for example the green dye often mixed with cooling fluid will fluoresce when illuminated. As per one embodiment of the invention, the illumination of the optical signal emitted by the light source is done at short wavelengths, since fluorescence is one property that is detected at longer wavelength than the excitation wavelength. The fluorescence 525 obtained from the fluid sample is typically weak since it has no preferential direction. In one embodiment of the apparatus, the optical signal emitted by the light source 515, having a short wavelength, is guided to the fluid sample flowing in the fluidic cavity 510 of the glass substrate 505 of the apparatus by at least one wave guide 535. To detect the fluorescence 525, at least one wave guide 520 is used that operates as a wavelength-selective splitter and separates the long wavelength fluorescent wavelength from the shorter wavelength excitation light signal. The optical detector 530 captures this wavelength and the fluorescence property is measured.

Figure 6:
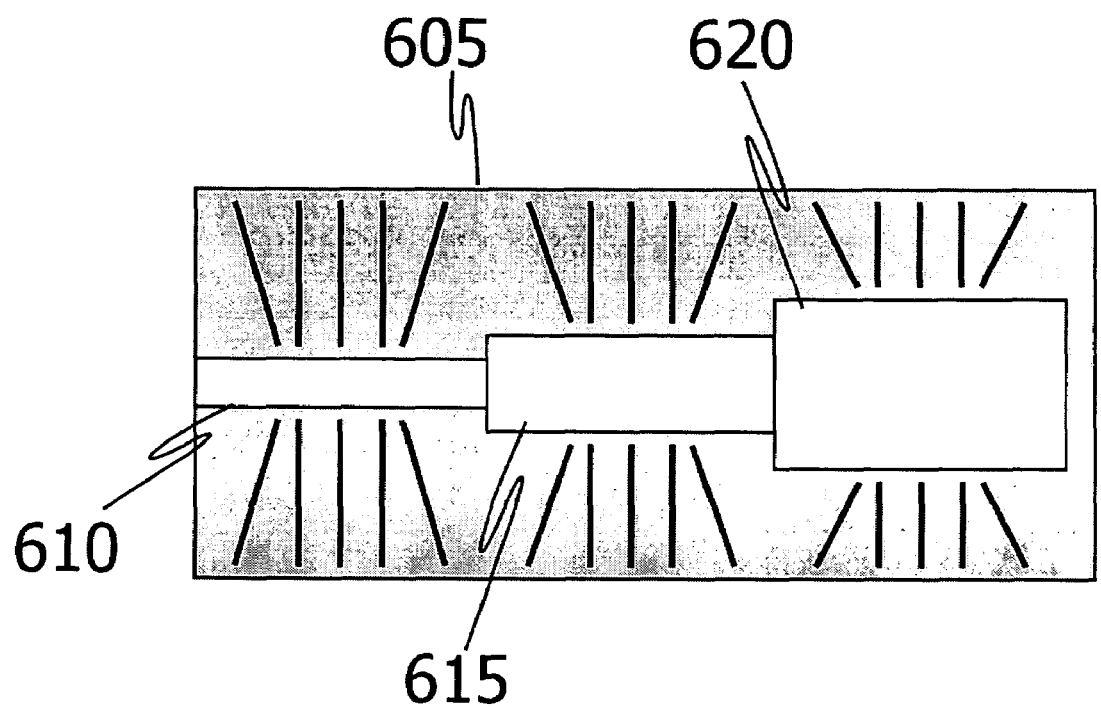
FIG. 6 is a schematic diagram for another embodiment of the apparatus demonstrating presence of multiple fluidic cavities.
Figure 7:
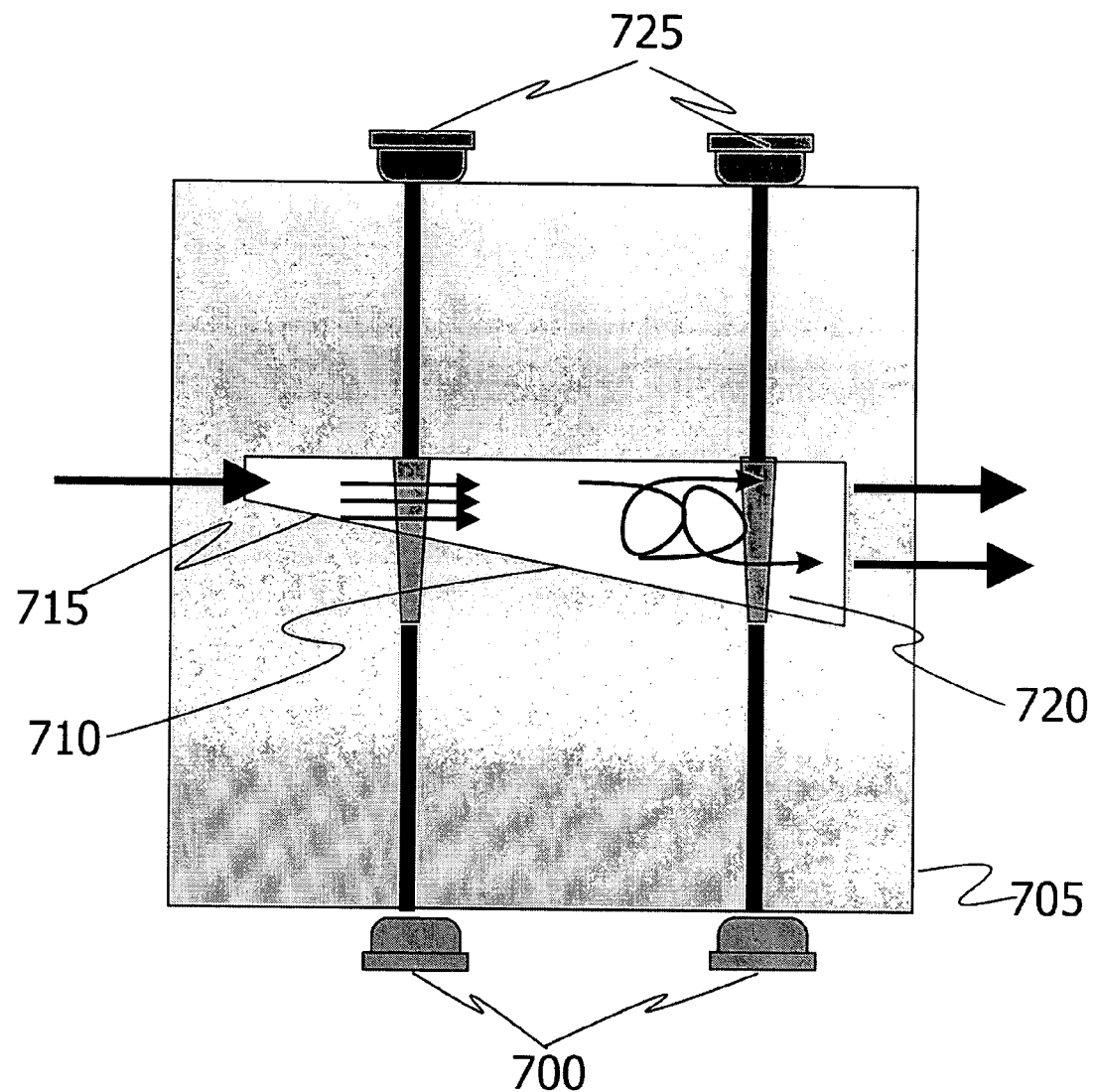
FIG. 7 is a schematic diagram for another embodiment of the apparatus demonstrating variations in width of the fluidic cavity.

As per another embodiment of the apparatus, as shown in FIG. 6, multiple fluidic cavities can be used for capturing the fluid sample within the apparatus for sensing the condition of the fluid. When the density of particulate impurity starts increasing in the fluid sample, i.e. multiple-particle scattering begins to occur due to high level of particulate contaminants in the fluid, the signal-to-noise ratio is reduced. Thus, the optical detectors may not capture the optical signal. However, by providing cavities of different widths 610, 615 and 620 within the substrate 605 of the apparatus, the signal-to-noise ratio is enhanced and the condition of the fluid can be sensed over a larger operational range of scattering densities. For example, when the fluid sample flows through the fluidic cavity 620, optical signals can face a high scattering density and be excessively weakened. The same fluid sample while flowing through the fluidic cavity 615 will have a lower scattering density in the area through which the fluid sample is flowing. This would increase the intensity of the optical signal. The fluidic cavity 610 will increase the response even further for the optical signal. Thus, by employing such an arrangement for the fluid sample, an accurate determination of the condition of the fluid can be made. In another embodiment of the apparatus, a single fluidic cavity of varying width can be used, as shown in FIG. 7. The fluidic cavity 710 within the substrate 705 for capturing the fluid sample is thin at the beginning 715 and rapidly increases in width at 720. Such an embodiment would serve similar benefits as discussed in FIG. 6. An optical signal emitted by the light source 700 is absorbed more at the position 720 as compared to the position 715, thereby, providing a different optimum measurement capability of the optical detector 725. Moreover, such an engineered fluidic cavity can ensure that the fluid sample flows in a laminar profile at 715 and becomes turbulent as it approaches the wider part of the fluidic cavity 720. A turbulent flow of the fluid sample within the fluidic cavity can ensure that no deposits take place inside the fluidic cavity. In another embodiment of the apparatus, the flow characteristics of the fluid sample are measured. In another embodiment of the apparatus, the flow characteristics such as Reynolds Number that can determine laminar or turbulent state of flow of the fluid sample can be measured. In another embodiment of the apparatus, the fluidic cavity can be shaped in a manner that enables filtering of particulate contamination from the fluid sample by trapping the particulates and for diverting the direction of the fluid sample. In another embodiment of the invention, the fluidic cavity can be created in a shape having a micro fluidic cavity. A width of the micro fluidic cavity is determined such that it prevents the entry of air bubbles within the micro fluidic cavity. The entry is prevented due to surface tension of the fluid sample that creates a vacuum within the micro fluidic cavity. Such an embodiment can eliminate measurement interferences due to air bubbles within the fluid sample.

Figure 8:
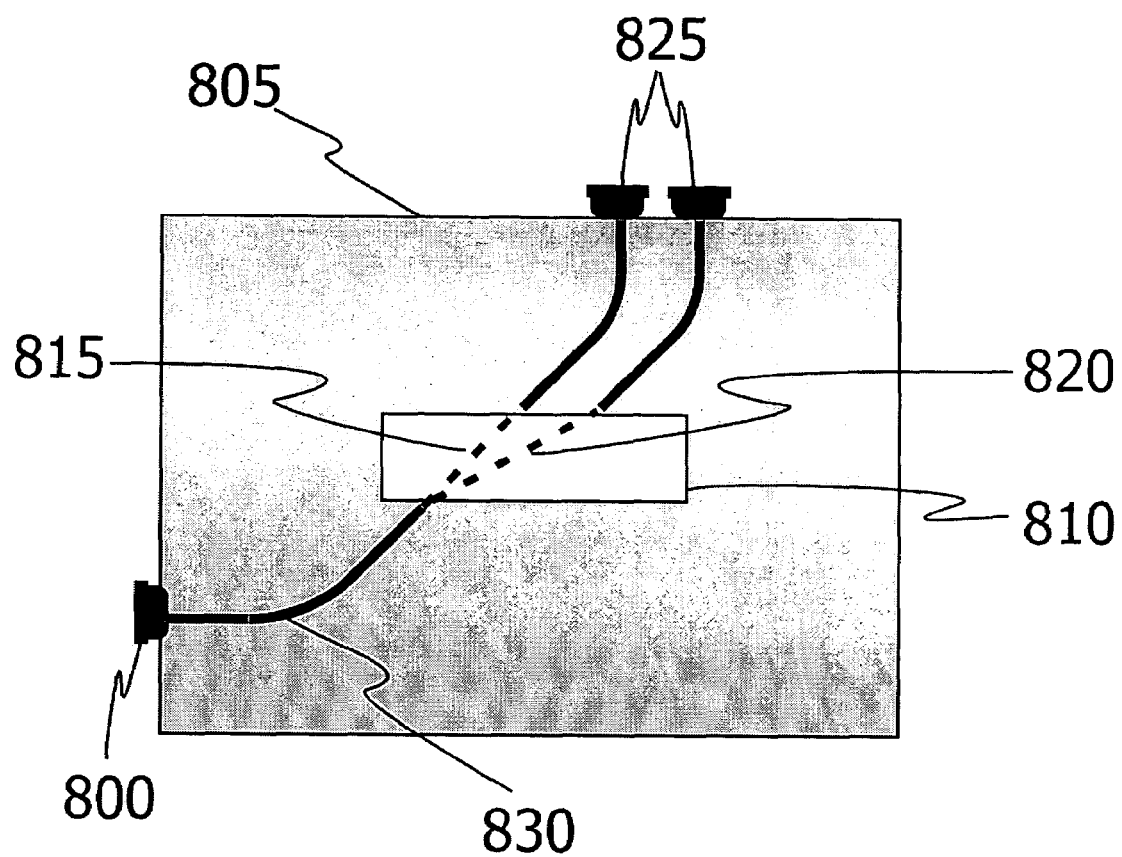
FIG. 8 is a schematic diagram for another embodiment of the apparatus demonstrating refraction measurement.

As per another embodiment of the apparatus, as shown in FIG. 8, to ascertain an existence of a fluid, a refraction of the optical signal is measured. An optical signal emitted by a light source 800 is guided through a wave guide 830 to a fluidic cavity 810 in a substrate 805 of the apparatus. In the absence of a fluid, the optical signal takes a path shown as 820. On the other, if the fluid exists, the optical signal takes a path shown as 815. This change occurs due to difference in refractive index of the glass substrate 805 and the fluid sample flowing in the fluidic cavity 810. The optical detector 825 collects the optical signal paths 815 and 820 and the deviation in the path of optical signal due to difference in refractive index is measured. This would help in determining the existence of a fluid that is being consumed in an industrial system. To determine the existence of the fluid, measurement of Luminous intensity, absorption or scattering values of the optical signal do not necessarily help in determining the presence or absence of the fluid.

Figure 9:
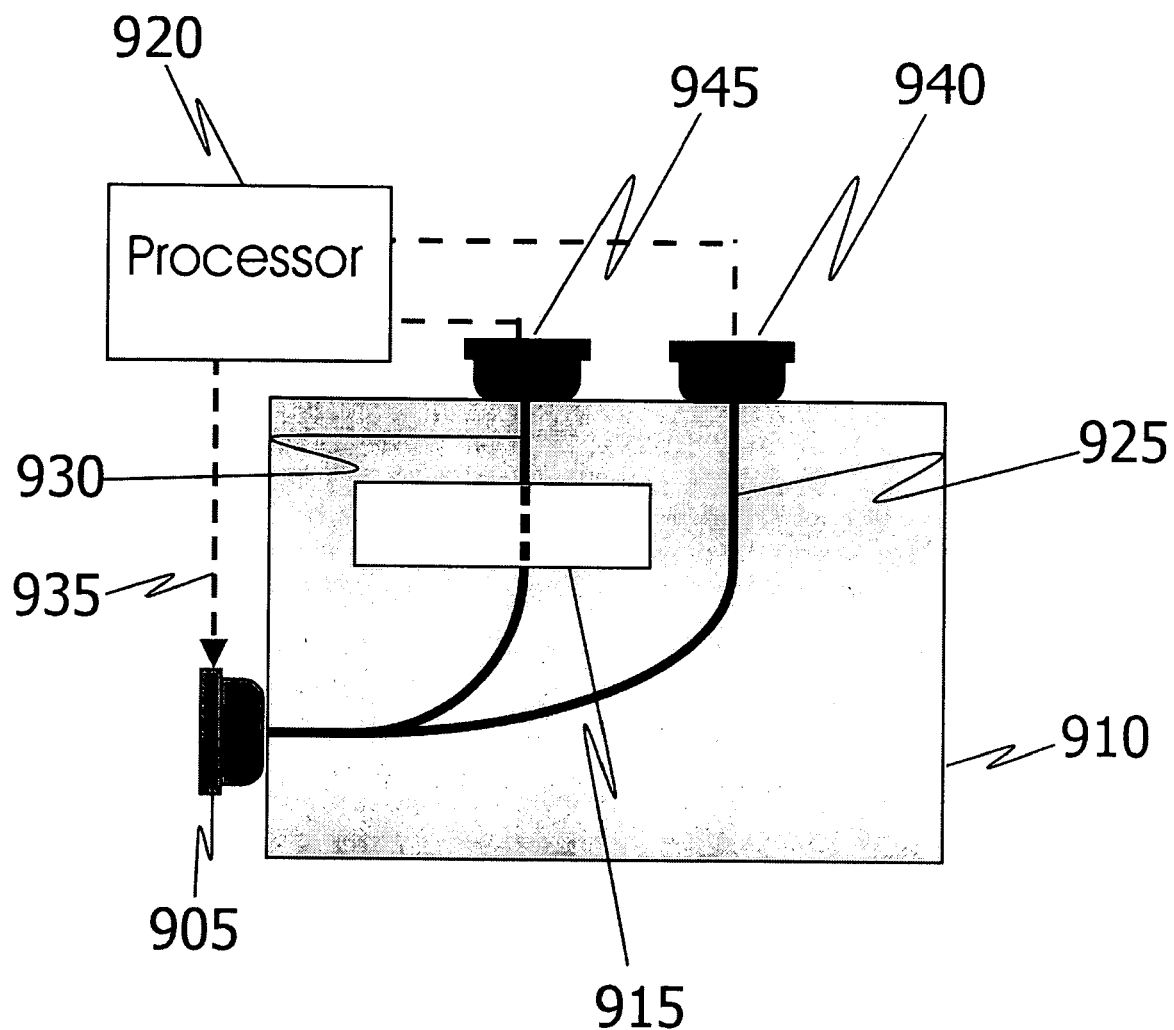
FIG. 9 is a schematic diagram for another embodiment of the apparatus for monitoring Luminous intensity of the optical signal.

As per another embodiment of the apparatus, as shown in FIG. 9, an electronic feedback 935 is provided to the light source 905 that emits the optical signal for controlling the Luminous intensity of the optical signal.

In one case, the stability of the optical signal generated by the light source 905 is monitored using a waveguide 925 and a detector 940. It is often a significant requirement that the Luminous intensity of the optical signal emitted by the light source 905 be kept at a constant 'Candela' value. A portion of the optical signal is sent to the optical detector 940 through a wave guide 925 avoiding the fluidic cavity 915 located in the substrate 910. Based on a comparison between the Luminous intensity value changes of the optical signal received by the optical detector 940 from the light source 905, an electronic feedback 935 is provided to the light source 905 on the Luminous intensity of the optical signal.

Alternatively one may measure the Luminous intensity of the signal at the output 925 and then correct the value of the intensity at the output 930.

In another case, if the signal received by the detector 945, is too weak to provide a reliable measurement of the condition of the fluid, a second electronic feedback is provided by the detector 945 to the light source 905 to increase the Luminous intensity value of the optical signal that the light source emits. When assessing the intensity of the optical signal, an evaluation is made whether the low signal condition is not created by a drift of light source 905 but rather by strong absorption or scattering within the cavity 915. In order to monitor the stability and the strength of the signal simultaneously, a logic element such as processor 920 is provided on the feedback loop to the light source 905.

Figure 10:
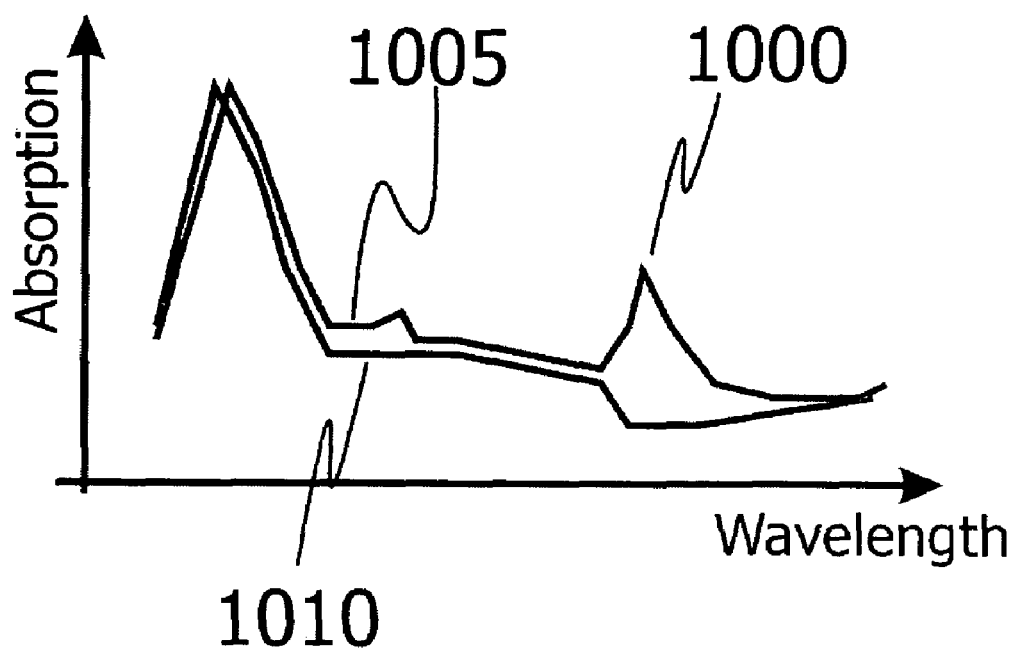
FIG. 10 is a graphical representation of variations of the absorption curve for the fluid with the wavelength of the optical signal.

FIG. 10 is a graphical representation of absorption detection method. Curve 1010 is an absorption curve for pure fluid. Curve 1005 is an absorption curve of the same fluid contaminated with water. The wavelength at which the kink in the absorption level of the curve 1005 shown at 1000 in FIG. 10 is obtained is the optimum wavelength for the optical signal emitted by the light source. At the wavelength corresponding to point 1000, the measurement of a difference between the absorption level of pure fluid and fluid contaminated with water is the maximum and most distinguishable.

Another embodiment of the invention further comprises a method for determining a fluid condition by collecting a fluid sample in-line from a fluid flow. Thereby, the fluid sample that is collected in a fluidic cavity is taken from a normal path of the fluid flow used in an industrial system. For example, there are some systems where there is a clear continuous fluid flow like oil pumped through a filter. In such cases, the fluid sample will be continuously collected in the fluidic cavity while the fluid is in motion. In other cases, the fluid sample may be present in the fluidic cavity, even when the fluid is not in motion. There are other systems where the flow is not continuous, for example, Hydraulic brake systems wherein the hydraulic fluid moves only when a force is applied to or removed from the brake pedal. Here the fluid sample is collected in the fluidic cavity whenever the fluid is set into motion. However, there are instances when the fluid sample is present in the fluidic cavity, when the fluid is not in motion. The method further comprises measuring a plurality of optical properties of the fluid sample simultaneously in real time. The collection of the fluid in-line enables making measurements in real time, i.e. measuring the change in optical properties of the fluid sample with time. In another embodiment, the method uses a light source emitting an optical signal and sending the optical signal through the fluid sample. In another embodiment, the optical signal is guided to the fluid sample through at least one first wave guide 155 as shown in FIG. 1. The method further comprises using an optical detector to capture the optical signal after the optical signal has passed through a fluid sample flowing through a fluidic cavity. In another embodiment, the optical signal is guided to the optical detector using at least one second wave guide 125 as shown in FIG. 1. In another embodiment, the method further comprises the optical detector providing a feedback to the light source to maintain a consistent Luminous intensity of the optical signal emitted by the light source. In another embodiment, measurement of the optical properties of the fluid sample by the optical detector involves measuring a Luminous intensity of the optical signal for Absorption, measuring a Luminous intensity of the optical signal after scattering and measuring a refraction value of the optical signal. In another embodiment, the method further comprises measuring a fluorescence of the optical signal. In another embodiment, the method further comprises measuring an electrical, a thermal and a magnetic property along with the optical properties.

Thus, the present invention allows a user to monitor the condition of a fluid in real time. The user can monitor the change in the condition of the fluid with time. The invention removes the complexities involved with the devices that use optical means to monitor the fluid condition and gives the user a simple method and apparatus that is capable of being integrated in-line with the system.

What is claimed is:

1. A method for determining a condition of a fluid flow, the method comprising:

directing a first optical signal to a fluid sample in a fluidic cavity in a glass block optically transparent to the first optical signal, wherein the fluidic cavity is connected in-line with the fluid flow;

guiding a second optical signal from the fluidic cavity via a glass waveguide region of the glass block, the second optical signal resulting from illumination of the fluid sample with the first optical signal;

capturing the second optical signal via a detector spaced from the fluidic cavity and coupled to the glass block to receive the second optical signal via the waveguide region; and, monitoring an optical property of the fluid sample based on the second optical signal to determine the condition of the fluid flow;

wherein the monitoring step comprises quantitatively measuring an intensity value of the second optical signal at the detector, and wherein the glass waveguide region is positioned such that the intensity value of the second optical signal is indicative of absorption of the first optical signal in the fluid flow.

2. The method of claim 1, wherein the directing step comprises:

emitting the first optical signal from a light source; and, sending the first optical signal through the glass block to reach the fluid sample.

3. The method of claim 2, wherein the sending step further comprises guiding the first optical signal from the light source to the fluid sample via a further waveguide region of the glass block.

4. The method of claim 2, further comprising the step of sending a further optical signal through the glass block via a further waveguide region of the glass block to provide feedback to the light source.

5. The method of claim 1, wherein the monitoring step comprises sensing variations in the optical property of the fluid sample continuously with respect to time.

6. The method of claim 1, wherein the monitoring step comprises quantitatively measuring an intensity of the second optical signal at a fluorescence wavelength resulting from excitation of the fluid sample by the first optical signal.

7. The method of claim 1, wherein the monitoring step comprises measuring the optical property at more than one location within the fluid sample in the fluidic cavity.

8. The method of claim 1, wherein the fluid cavity has a varying shape to control a flow characteristic of the fluid sample.

9. The method of claim 8, wherein the flow characteristic is the Reynolds number of the fluid sample.

10. The method of claim 1, wherein the fluid flow comprises an engine fluid.

11. The method of claim 1, wherein the optical property monitoring step comprises determining a contaminant level of the fluid flow.

12. The method of claim 11, wherein the determining step comprises detecting optical absorption arising from particulate impurities in the fluid flow.

13. The method of claim 1, wherein the fluid flow comprises a hydraulic fluid.

14. A method for determining a condition of a fluid flow, the method comprising:
   directing a first optical signal to a fluid sample in a fluidic cavity in a glass block optically transparent to the first optical signal, wherein the fluidic cavity is connected in-line with the fluid flow;
   guiding a second optical signal from the fluidic cavity via a glass waveguide region of the glass block, the second optical signal resulting from illumination of the fluid sample with the first optical signal;
   capturing the second optical signal via a detector spaced from the fluidic cavity and coupled to the glass block to receive the second optical signal via the waveguide region; and,
   monitoring an optical property of the fluid sample based on the second optical signal to determine the condition of the fluid flow;
   wherein the monitoring step comprises quantitatively measuring an intensity value of the second optical signal at the detector, and wherein the glass waveguide region is positioned such that the intensity value of the second optical signal is indicative of a change in refraction of the first optical signal resulting from the first optical signal entering the fluid sample.

15. A system for determining a condition of a fluid flow, the system comprising:
   a glass block;
   a fluidic cavity in the glass block configured to be connected in-line with the fluid flow to collect a fluid sample of the fluid flow;
   a light source positioned relative to the glass block and configured to emit a first optical signal for illumination of the fluid sample; and
   a detector spaced from the fluidic cavity and coupled to the glass block to receive a second optical signal resulting from the illumination of the fluid sample to quantitatively measure an intensity value of the second optical signal to determine the condition of the fluid flow;
   wherein a glass waveguide region of the glass block is configured to guide the second optical signal from the fluidic cavity to the detector, wherein the glass block is optically transparent to the first and second optical signals, and wherein the glass waveguide region is positioned such that the second optical signal is indicative of absorption of the first optical signal in the fluid flow.

16. The system of claim 15, wherein the light source comprises a Light Emitting Diode or a Diode Laser.

17. The system of claim 15, further comprising a further waveguide region of the glass block configured to guide the first optical signal from the light source to the fluid sample.

18. The system of claim 15, further comprising a lens coupled to the glass block and configured to collimate the first optical signal.

19. The system of claim 15, wherein a further waveguide region of the glass block is configured to guide a feedback optical signal through the glass block to provide feedback to the light source.

20. The system of claim 15, further comprising a wavelength-selective splitter in the glass block and coupled to the waveguide region to separate the first optical signal from the second optical signal, wherein the second optical signal is at a fluorescence wavelength resulting from excitation of the fluid sample by the first optical signal.

21. The system of claim 15, wherein the fluid cavity has a varying shape.

22. A system for determining a condition of a fluid flow, the system comprising:
   a glass block;
   a fluidic cavity in the glass block configured to be connected in-line with the fluid flow to collect a fluid sample of the fluid flow;
   a light source positioned relative to the glass block and configured to emit a first optical signal for illumination of the fluid sample; and
   a detector spaced from the fluidic cavity and coupled to the glass block to receive a second optical signal resulting from the illumination of the fluid sample to quantitatively measure an intensity value of the second optical signal to determine the condition of the fluid flow;
   wherein a glass waveguide region of the glass block is configured to guide the second optical signal from the fluidic cavity to the detector, wherein the glass block is optically transparent to the first and second optical signals, and wherein the glass waveguide region is positioned such that the second optical signal is indicative of a change in refraction of the first optical signal resulting from the first optical signal entering the fluid sample.

23. A system for determining a condition of a fluid flow, the system comprising:
   a glass block;
   a fluidic cavity in the glass block configured to be connected in-line with the fluid flow to collect a fluid sample of the fluid flow;
   a light source positioned relative to the glass block and configured to emit a first optical signal for illumination of the fluid sample; and
   a detector spaced from the fluidic cavity and coupled to the glass block to receive a second optical signal resulting from the illumination of the fluid sample to quantitatively measure an intensity value of the second optical signal to determine the condition of the fluid flow;
   wherein a glass waveguide region of the glass block is configured to guide the second optical signal from the fluidic cavity to the detector, wherein the glass block is optically transparent to the first and second optical signals, and wherein the glass waveguide region is positioned such that the second optical signal is indicative of scattering of the first optical signal by particulate impurities in the fluid sample such that the condition of the fluid flow reflects a contaminant level.

24. The system of claim 23, wherein the waveguide region is positioned such that the second optical signal is indicative of back scattering of the first optical signal by the particulate impurities in the fluid sample such that the condition of the fluid flow reflects the contaminant level.

25. A method for determining a condition of a fluid flow, the method comprising:
   directing a first optical signal to a fluid sample in a fluidic cavity in a glass block optically transparent to the first optical signal, wherein the fluidic cavity is connected in-line with the fluid flow;
   guiding a second optical signal from the fluidic cavity via a glass waveguide region of the glass block, the second optical signal resulting from illumination of the fluid sample with the first optical signal;

capturing the second optical signal via a detector spaced from the fluidic cavity and coupled to the glass block to receive the second optical signal via the waveguide region; and, monitoring an optical property of the fluid sample based on the second optical signal to determine the condition of the fluid flow;

wherein the monitoring step comprises quantitatively measuring an intensity value of the second optical signal at the detector, and wherein the glass waveguide region is positioned such that the intensity value of the second optical signal is indicative of scattering of the first optical signal by the fluid sample.

26. The method of claim 25, wherein the waveguide region is positioned such that the intensity value of the second optical signal is indicative of the first optical signal being back scattered while passing through the fluid sample.

* * * * *